(12) United States Patent
Cho et al.

(10) Patent No.: US 11,246,528 B2
(45) Date of Patent: Feb. 15, 2022

(54) SYSTEM FOR MONITORING AND DIAGNOSING SLEEP-DISORDERED BREATHING BY USING DRUG INDUCED SLEEP ENDOSCOPY AND METHOD FOR MONITORING AND DIAGNOSING SLEEP-DISORDERED BREATHING

(71) Applicant: PHAROS CO., LTD., Gwangju (KR)

(72) Inventors: Hyong Ho Cho, Gwangju (KR); Hyung Chae Yang, Gwangju (KR); Sung Su Lee, Gwangju (KR)

(73) Assignee: PHAROS CO., LTD., Gwangju (KR)

( * ) Notice: Subject to any disclaimer, the term of this patent is extended or adjusted under 35 U.S.C. 154(b) by 357 days.

(21) Appl. No.: 16/491,356

(22) PCT Filed: Nov. 17, 2017

(86) PCT No.: PCT/KR2017/013074
§ 371 (c)(1),
(2) Date: Sep. 5, 2019

(87) PCT Pub. No.: WO2018/164342
PCT Pub. Date: Sep. 13, 2018

(65) Prior Publication Data
US 2021/0298665 A1   Sep. 30, 2021

(30) Foreign Application Priority Data

Mar. 7, 2017   (KR) .................. 10-2017-0028788

(51) Int. Cl.
*A61B 5/318*   (2021.01)
*A61B 5/00*    (2006.01)
(Continued)

(52) U.S. Cl.
CPC .......... *A61B 5/4818* (2013.01); *A61B 1/0005* (2013.01); *A61B 1/24* (2013.01);
(Continued)

(58) Field of Classification Search
CPC ....... A61B 1/0005; A61B 1/24; A61B 5/1114; A61B 5/1116; A61B 5/14542;
(Continued)

(56) References Cited

U.S. PATENT DOCUMENTS

2015/0306340 A1* 10/2015 Giap .................. A61B 6/461
600/301

FOREIGN PATENT DOCUMENTS

JP   2002-345781 A   12/2002
JP   2006-000536 A    1/2006
(Continued)

OTHER PUBLICATIONS

International Search Report for PCT/KR2017/013074 dated Mar. 22, 2018.

*Primary Examiner* — George Manuel
(74) *Attorney, Agent, or Firm* — The PL Law Group, PLLC

(57) ABSTRACT

A monitoring and diagnosing system includes a position indication instruction device, an endoscope equipment, and an image integrated monitoring device. The system may be capable of increasing reliability of a test by performing drug induced sleep endoscopy while changing, in a predetermined order, a body position of a patient so as to examine sleep-disordered breathing.

19 Claims, 6 Drawing Sheets

(51) Int. Cl.
    *A61B 1/00*     (2006.01)
    *A61B 1/24*     (2006.01)
    *A61B 5/11*     (2006.01)
    *A61B 5/145*     (2006.01)
    *A61B 7/00*     (2006.01)

(52) U.S. Cl.
    CPC ........... *A61B 5/1114* (2013.01); *A61B 5/1116* (2013.01); *A61B 5/14542* (2013.01); *A61B 5/318* (2021.01); *A61B 5/746* (2013.01); *A61B 7/003* (2013.01)

(58) Field of Classification Search
    CPC ..... A61B 5/1455; A61B 5/318; A61B 5/4818; A61B 5/742; A61B 5/746; A61B 7/003
    See application file for complete search history.

(56) References Cited

FOREIGN PATENT DOCUMENTS

| | | |
|---|---|---|
| JP | 2010-131406 A | 6/2010 |
| KR | 10-2010-0036420 A | 4/2010 |
| KR | 10-2014-0145091 A | 12/2014 |

\* cited by examiner

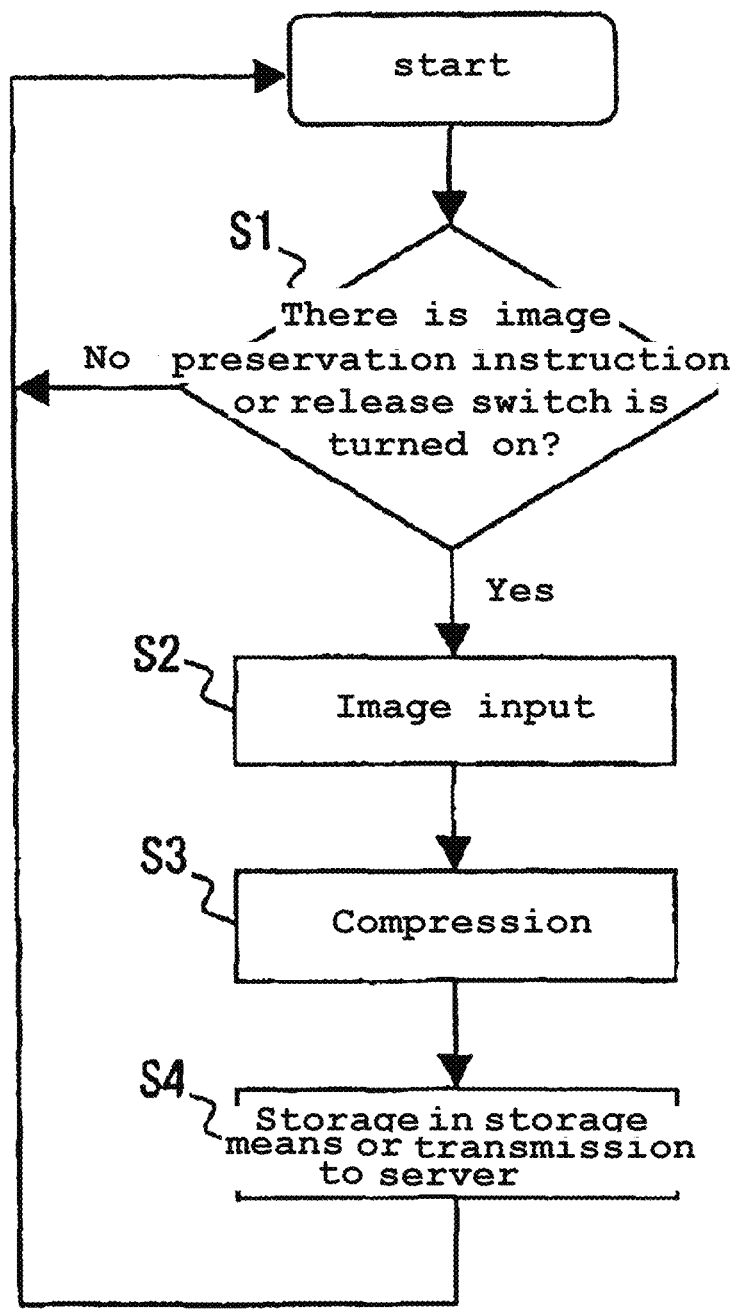

SYSTEM FOR MONITORING AND DIAGNOSING SLEEP-DISORDERED BREATHING BY USING DRUG INDUCED SLEEP ENDOSCOPY AND METHOD FOR MONITORING AND DIAGNOSING SLEEP-DISORDERED BREATHING

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2017/013074, filed Nov. 17, 2017, which claims priority to the benefit of Korean Patent Application No. 10-2017-0028788 filed in the Korean Intellectual Property Office on Mar. 7, 2017, the entire contents of which are incorporated herein by reference.

TECHNICAL FIELD

The present invention relates to a drug induced sleep endoscopy system-related technology and, more particularly, to a system for monitoring and diagnosing sleep-disordered breathing and a method for monitoring and diagnosing sleep-disordered breathing, the system and method being capable of increasing reliability of a test by performing drug induced sleep endoscopy while changing, in a predetermined order, a body position of a patient so as to examine sleep-disordered breathing.

BACKGROUND ART

In general, obstructive sleep apnea (OSA) is associated with sleep-disordered breathing, it is a disease that leads to night hypoxia and daytime sleepiness by repeatedly obstructing a part or all of the upper airway during sleep. Chronic hypoxia leads to inflammatory cytokines, sympathetic nerves, endothelial dysfunction, and increased cardiovascular mortality.

Obstructive sleep apnea or snoring may occur due to obstruction of various parts such as nasal cavity, pharynx, hypopharyngeal, larynx and epiglottis in addition to the palatal area. The site and the degree of obstruction are significantly different from each other in the state of sleep and wakefulness, and show various changes due to changes in the position of the patient, the position of the lower jaw, and the like.

Therefore, in order to treat obstructive sleep-disordered breathing, since the accurate operation of the obstructive part is very important factor for the success of the operation, a diagnosis method for identifying the accurate obstructive site is needed first.

On the other hand, drug-induced sleep endoscopy test is a method to examine the site of obstruction by using a flexible laryngoscopy commonly used in otolaryngology, after inducing artificial sleep using drugs.

The drug-induced sleep endoscopy test using common flexible laryngoscopy for otolaryngology, which has been used to date, makes it possible to observe or reproduce the airway at the time of induction of sleep, but makes it impossible to check the vital signs of the patient, the patient's sleep, the patient's posture, the degree of snoring, and the behavior of the medical staff when the fluid changes in the airway form shows a certain appearance.

In order to solve the problem, there is a need for endoscope equipment capable of showing and recording at least one of a patient's posture, a snoring degree, and a vital sign corresponding to a part of the patient's body cavity and the situation during the sleep-induced endoscopy, but there is no equipment for this to date.

SUMMARY

The present inventor have developed a monitoring and diagnostic technique that simultaneously displays and stores an intracorporeal image taken by a drug induced sleep endoscopy device and an extracorporeal image obtained by capturing a patient's specific position.

Accordingly, an objective of the present invention is to provide a monitoring and diagnosing system and method, in which during drug induced sleep endoscopy, an intracorporeal image of the part of the patient's body cavity captured by the drug induced sleep endoscopy device, and patient position information and/or an extracorporeal image obtained by capturing the patient's specific position at a point of time when the intracorporeal image is captured are displayed on a display device and stored to be simultaneously recognized, so that it is possible to safely and accurately diagnose the obstructed part of the upper airway that is the cause of snoring or sleep apnea and to set treatment directions and patient education on the basis of the same, when treating a patient with sleep-disordered breathing such as snoring or sleep apnea in otolaryngology, psychiatry, neurology, or respiratory clinics.

Another objective of the present invention is to provide a monitoring and diagnosing system and method, in which a standardized test protocol can be provided so that patient position information is sequentially displayed in a predetermined order on the display device so that drug induced sleep endoscopy is performed while changing the position of the patient in the predetermined order, to allow a physician performing the drug induced sleep endoscopy to perform endoscopy on each necessary patient position without exception, in order to accurately diagnose sleep-disordered breathing, considering that it is necessary to monitor an intracorporeal image obtained by capturing a part in the patient's body cavity with endoscope equipment for each position while the patient takes a plurality of body positions.

Still another object of the present invention is to provide a vital sign monitoring and diagnosing system and method of allowing a patient who is sleeping during drug-induced endoscopy to be managed immediately even if apnea related serious adverse event occurs in the patient due to drugs.

Still another object of the present invention is to provide a monitoring and diagnosing system and method that captures the behavior of a physician performing drug induced sleep endoscopy so as to control inappropriate behavior of the physician occurring during the drug induced sleep endoscopy procedure.

The object of the present invention is not limited to the above-mentioned object, and even if not explicitly mentioned, the object of the invention that can be recognized by those skilled in the art from the description of the detailed description of the invention following can be included.

In order to achieve the above objectives, the present invention provides a monitoring and diagnosing system including: a position indication instruction device instructing to display patient position information necessary for a drug-induced sleep endoscopic procedure on a partial region of a display device during the drug-induced sleep endoscopic procedure, that is to be performed several times for each position while changing a patient body position; an endoscope equipment inserted into a body cavity of a patient taking a body position suitable for the patient position information displayed on the display device to capture an intracorporeal image of the patient; and an image integrated monitoring device receiving the patient position information to display the patient position information on a partial region of the display device and then receiving the intracorporeal image to output the intracorporeal image on a region including or excluding the partial region of the display device, thereby displaying the intracorporeal image and the patient position information to be simultaneously recognized and storing the intracorporeal image and the patient position information as a test file to be simultaneously recognized.

In a preferable embodiment, the position indication instruction device may be controlled so that first patient position information required for the drug-induced sleep endoscopic procedure is displayed according to a predetermined order when a start signal is input by a procedural physician performing the drug induced sleep endoscopy and next patient position information is sequentially displayed when a next signal is input.

In a preferable embodiment, the position indication instruction device may be configured as a foot switch stepped on by a procedure physician performing the drug induced sleep endoscopy.

In a preferable embodiment, the patient position information may be one selected from a group consisting of Supine (posture of a patient lying down looking at a ceiling), Chin lift & jaw thrust (posture of a patient lifting chin and thrusting jaw), Head turning to left (posture of a patient turning head to left), and Head turning to right (posture of a patient turning head to right).

In a preferable embodiment, the monitoring and diagnosing system may further include an extracorporeal image capturing device capturing, as an extracorporeal image, a specific change in the patient body position occurring in correspondence to a point of time when the endoscope equipment captures a specific part in the body cavity as the intracorporeal image.

In a preferable embodiment, the image integrated monitoring device may receive the extracorporeal image from the extracorporeal image capturing device to output and display the extracorporeal image for the change in the patient body position simultaneously on the display device to be corresponded to the intracorporeal image of the specific part in the body cavity, and stores the intracorporeal image, the extracorporeal image, and the patient position information as a test file to be simultaneously recognized.

In a preferable embodiment, the monitoring and diagnosing system may further include a snoring analysis device recording a snoring sound of the patient undergoing the drug induced sleep endoscopy and generating a waveform to form a snoring analysis image.

In a preferable embodiment, the monitoring and diagnosing system may further include a detection device detecting and analyzing a vital sign of the patient during the endoscopic procedure.

In a preferable embodiment, the detection device may detect and analyze one or more of oxygen saturation and electrocardiogram.

In a preferable embodiment, the monitoring and diagnosing system may further include a monitoring device capturing a physician behavior image including behavioral changes of the procedural physician performing the drug induced sleep endoscopy.

In a preferable embodiment, the image integrated monitoring device may further receive one or more of the intracorporeal image, any one or more of the patient position information and the extracorporeal image, a physician behavior image of the procedural physician performing the drug induced sleep endoscopy, and a snoring analysis image and a vital sign analysis image of the patient undergoing the drug induced sleep endoscopy to be outputted on the display device simultaneously.

In a preferable embodiment, the image integrated monitoring device may receive an input signal according to a determination of the procedural physician performing the drug induced sleep endoscopy and then stores the test file as one or more diagnostic files including images at a point of time necessary for sleep-disordered breathing diagnosis.

In a preferable embodiment, the diagnostic file may include any one or more of the intracorporeal image, the patient position information, and the extracorporeal image corresponding to a point of time when the input signal is received.

In a preferable embodiment, the monitoring and diagnosing system may further include: when apnea occurs in a patient who is sleeping during the drug-induced sleep endoscopic procedure, a warning unit informing the physician performing the procedure that the patient in apnea to treat the patient immediately.

In addition, the present invention provides a monitoring and diagnosing method of sleep-disordered breathing, the method including: a drug-induced sleep endoscopic procedure step including displaying predetermined patient position information on a display device according to a signal input from a position indication instruction device, displaying an intracorporeal image captured by endoscope equipment in an upper airway of a patient taking a position appropriate for the patient position information, separately from or to be overlapped with the patient position information on the display device, and storing the intracorporeal image and the patient position information as a test file to be recognized simultaneously; and repeating the drug induced sleep endoscopic procedure step a number of times that is one less than the number of pieces of the predetermined patient position information according to an order of the predetermined patient position information.

In a preferable embodiment, the drug induced sleep endoscopic procedure step may further include: capturing, as an extracorporeal image, a specific change of a patient position occurring in correspondence to a point of time when the endoscope equipment captures a specific part in the upper airway as the intracorporeal image, by an extracorporeal image capturing device; and displaying the captured extracorporeal image on the display device to be recognized simultaneously with the intracorporeal image and storing the captured extracorporeal image as the test file to be recognized simultaneously with the intracorporeal image.

In a preferable embodiment, the drug induced sleep endoscopic procedure step further includes: recording a snoring sound of a patient occurring in correspondence to a point of time when the endoscope equipment captures a specific part in the upper airway as the intracorporeal image and generating a waveform to obtain a snoring analysis image, by a snoring analysis device; and displaying the snoring analysis image on the display device to be recognized simultaneously with the intracorporeal image and the patient position information and storing the snoring analysis image as the test file to be recognized simultaneously with the intracorporeal image and the patient position information.

In a preferable embodiment, the drug induced sleep endoscopic procedure step may further include: detecting and analyzing a vital sign of a patient occurring in correspondence to a point of time when the endoscope equipment captures a specific part of the upper airway as the intracorporeal image to generate a vital sign analysis image, by a detection device; and displaying the generated vital sign analysis image on the display device to be recognized simultaneously with the intracorporeal image and the patient position information, and storing the generated vital sign analysis image as the test file to be recognized simultaneously with the intracorporeal image and the patient position information.

In a preferable embodiment, the test file may be a diagnostic file including the intracorporeal image, and any one or more of the position indication information and the extracorporeal image, which correspond to a point of time when an input signal is received according to a determination of a procedure physician performing the drug induced sleep endoscopy.

According to an embodiment of the present invention, during the drug induced sleep endoscopy, an intracorporeal image of the part of the patient's upper airway captured by the drug induced sleep endoscopy device, and patient position information and/or an extracorporeal image obtained by capturing the patient's specific position at a point of time when the intracorporeal image is captured are displayed on a display device and stored to be simultaneously recognized, whereby it is possible to safely and accurately diagnose the obstructed part of the body cavity that is the cause of snoring or sleep apnea and to set treatment directions and patient education on the basis of the same, when treating a patient with sleep-disordered breathing such as snoring or sleep apnea in otolaryngology, psychiatry, neurology, or respiratory clinic.

In addition, according to the present invention, it is possible to provide an image of accurately diagnosing sleep-disordered breathing, so that even when a sleep apnea surgeon and a sleep-disordered breathing examiner are different from each other, the physician can plan and perform the surgery using the stored image without retesting, and accordingly medical expenses can be reduced, patient discomfort due to retesting can be alleviated, and test efficiency can be improved.

In addition, according to the present invention, it is possible to provide a standardized test protocol so that patient position information is sequentially displayed in a predetermined order on the display device so that drug induced sleep endoscopy is performed while changing the position of the patient in the predetermined order, to allow a physician performing the drug induced sleep endoscopy to perform endoscopy on each necessary patient position without exception, in order to accurately diagnose sleep-disordered breathing, considering that it is necessary to monitor an intracorporeal image obtained by capturing a part in the patient's upper airway with endoscope equipment for each position while the patient takes a plurality of body positions.

In addition, according to the present invention, it is possible to provide a monitoring and diagnosing system and method of allowing a patient who is sleeping during drug-induced endoscopy to be treated immediately even if apnea occurs in the patient due to drugs.

In addition, according to the present invention, it is possible to provide a monitoring and diagnosing system and method that captures the behavior of a physician performing drug induced sleep endoscopy so as to control inappropriate behavior of the physician occurring during the drug induced sleep endoscopy procedure.

These technical effects of the present invention are not limited to the above-mentioned range, and although not explicitly mentioned, the invention can be recognized by those skilled in the art from the description of the specific contents for the practice of the invention described below.

BRIEF DESCRIPTION OF THE DRAWINGS

FIG. 2b is an implementation example of a position indication instruction device instructing that the patient position information is displayed on the display device in a monitoring and diagnosing system according to the predetermined patient position information protocol shown in FIG. 2a.

FIG. 5 is a flowchart illustrating a process of generating a diagnosis file in the system of FIG. 1.

MODE FOR INVENTION

Figure 1:
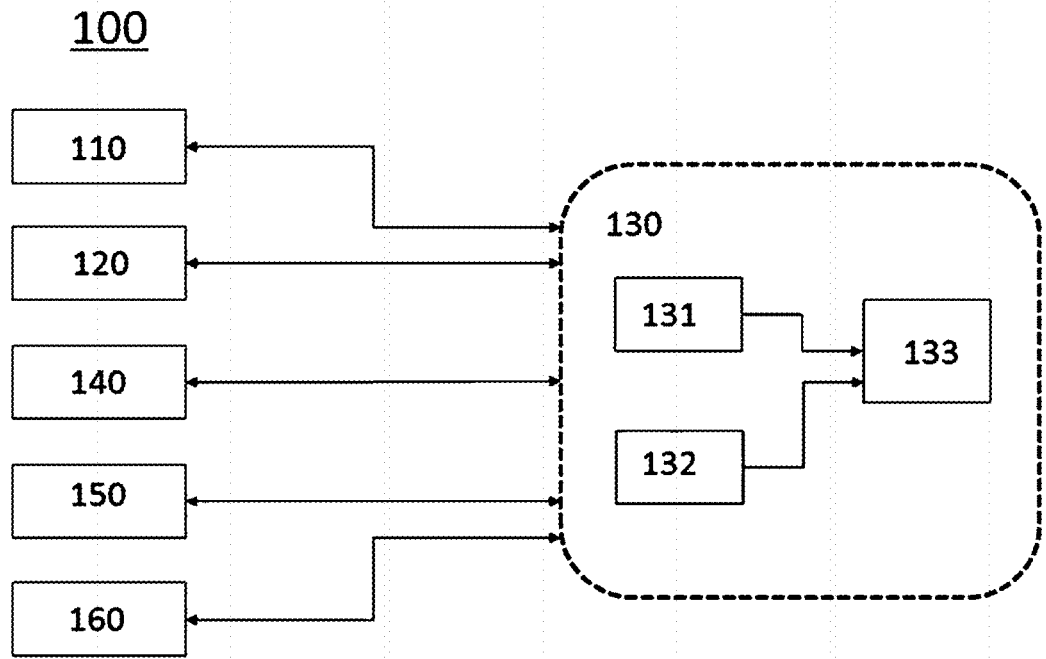
FIG. 1 is a block diagram of a monitoring and diagnosing system according to an embodiment of the present invention.

The terms used in the present invention have been selected as widely used general terms as possible in consideration of the functions in the present invention, but may vary according to the intention or precedent of the person skilled in the art, the emergence of new technologies, and the like. In addition, in certain cases, there is also a term arbitrarily selected by the applicant, in which case the meaning will be described in detail in the description of the invention. Therefore, the terms used in the present invention should be interpreted on the basis of the general meaning of the term rather than simply the name of the term, and the contents described throughout the specification of the present invention.

In particular, when the degree of terms "about", "substantially", and the like are used, they are interpreted as being used in or near the numerical value when a manufacturing and material tolerance unique to the stated meaning is given. Singular expressions include plural expressions unless the context clearly indicates otherwise. In this application, the terms "comprises" or "having" are intended to indicate that there is a feature, number, step, action, component, part, or combination thereof described in the specification, and it should be understood that it does not exclude in advance the possibility of the presence or addition of one or more other features, or numbers, steps, actions, components, parts or combinations thereof. Terms such as first and second may be used to describe various components, but the components should not be limited by the terms. The terms are used only for the purpose of distinguishing one component from another. For example, without departing from the scope of the present invention, the first component may be referred to as the second component, and similarly, the second component may also be referred to as the first component.

Hereinafter, with reference to the accompanying drawings and preferred embodiments will be described in detail the technical configuration of the present invention.

However, the present invention is not limited to the embodiments described herein and may be embodied in other forms. Like reference numerals used to describe the present invention throughout the specification denote like elements.

Technical features of the present invention is a monitoring and diagnosing system and method, in which an intracorporeal image of a part in the patient's upper airway captured by the drug induced sleep endoscopy device during the progress of the drug induced sleep endoscopy, and the body position information and/or an extracorporeal image obtained by capturing a specific body position of the patient at the time of capturing the upper airway image are displayed on the display means and stored to be simultaneously recognized, whereby it is possible to safely and accurately diagnose the obstructed part of the upper airway which is a cause of sleep-disordered breathing and thus to set the treatment direction and perform the patient education on the basis of the diagnosis results.

In particular, the monitoring and diagnosing system of the present invention enables performance of drug induced sleep endoscopy while changing the body position of the patient according to a predetermined order displayed on the display device by sequentially displaying the patient position information in the predetermined order on the display device, whereby it is possible to provide a standardized test protocol that a physician performing drug induced sleep endoscopy may perform drug induced sleep endoscopy on each body position of a patient without exception. In other words, in order to accurately diagnose sleep-disordered breathing, it is necessary to monitor an intracorporeal image obtained by capturing a patient's upper airway area for each body position via endoscopic equipment while the patient takes a plurality of specific body positions.

As is known, the drug-induced drug induced sleep endoscopy test is a test necessary for the surgical treatment of patients with sleep apnea or snoring, and is generally performed by an examination physician separate from the outpatient physician and in a room separate from an outpatient examination room, or an endoscope room, after anesthetizing the patient with propofol, etc. The drug-induced sleep endoscopy is a procedure that determines the changes in an upper airway in response to changes in body position during sleep and wakefulness, in which the airway is first determined before sleep induction, and then the airway state is determined after performing sleep-inducing using drugs, unlike the gastroscope. In addition, various position changes are made for each sleep state, and correspondingly each airway state should be determined. In other words, it is important to check what body position the patient is in when a physician monitors the airway state which is a patient's upper airway area observed on the screen.

In addition, the patient in a trance immediately after the test may not consult with the doctor, the consultation relating to the test result is usually conducted as the outpatient after a period of time. Records and regeneration of the accurate procedure are required for proper consultation and decision making with patients or guardians. However, since the recording screen using a flexible laryngoscopy for general otorhinolaryngology currently used enables only checking of the airway screen using the endoscope, there is a problem that it is difficult for the doctor to explain, to the patient, the change in the airway and the lesion site according to various body position changes and examination methods.

Meanwhile, according to the present invention, after the drug induced sleep endoscopy test, the location of the upper respiratory system obstruction may be known with only data informing what body position the patient is in, so that it is possible to improve the reliability of the test and accurately determine the lesion site than the reading by the subjective memory of the examiner, whereby the treatment may be easily planned and usefully used for postoperative observation after surgery. In addition, there is no need for a recorder at the time of examination, which saves manpower. In addition, it is useful not only to help education and disease understanding of the patient after the examination, but also to provide information when the examiner and the operator of the surgery are different from each other.

Therefore, the monitoring and diagnosing system according to the present invention includes a position indication instruction device instructing that patient position information is displayed on a display device, an endoscope equipment inserted into the upper airway of the patient to capture the intracorporeal image of the patient, and an image integrated monitoring device receiving the patient position body information and the intracorporeal image to simultaneously output the same to the display device and store the same as test files. As necessary, the monitoring and diagnosing system further includes one or more of an extracorporeal image recording device recording, as an extracorporeal image, a specific positional change of the patient occurring in correspondence to the recording time of the intracorporeal image, snoring analysis device forming a snoring analysis image of the patient, a detection device detecting and analyzing a vital sign of the patient, a monitoring device capturing the procedural physician behavior image, and a warning means informing the doctor during the surgical procedure that the patient is in apnea.

In addition, monitoring and diagnosing method of sleep-disordered breathing includes a drug-induced sleep endoscopic procedure step including displaying predetermined patient position information on a display device according to a signal input from a position indication instruction device, displaying an intracorporeal image captured by endoscope equipment in an upper airway of a patient taking a position appropriate for the patient position information, separately from or to be overlapped with the patient position information on the display device, and storing the intracorporeal image and the patient position information as a test file to be recognized simultaneously; and repeating the drug-induced sleep endoscopic procedure step a number of times that is one less than the number of pieces of the predetermined patient position information according to an order of the predetermined patient position information.

Specific embodiments according to an embodiment of the present invention will be described in detail with reference to the drawings.

Figure 2A:
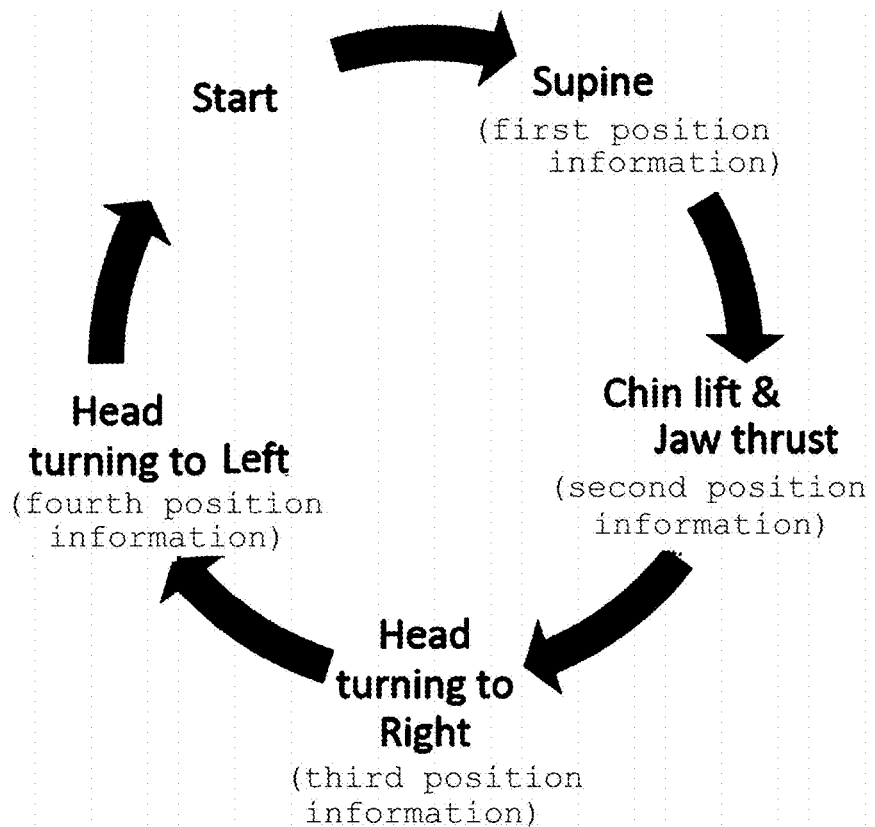
FIG. 2a is a flowchart of an implementation example illustrating a predetermined patient position information protocol to be instructed by a position indication instruction device in the monitoring and diagnosing system of the present invention.
Figure 2B:
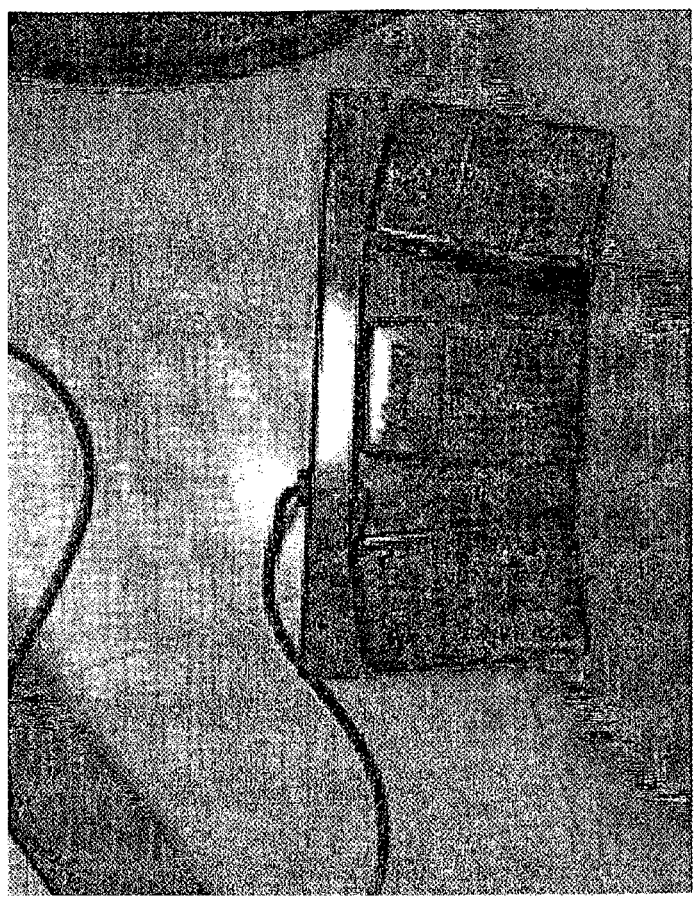
Figure 3A:
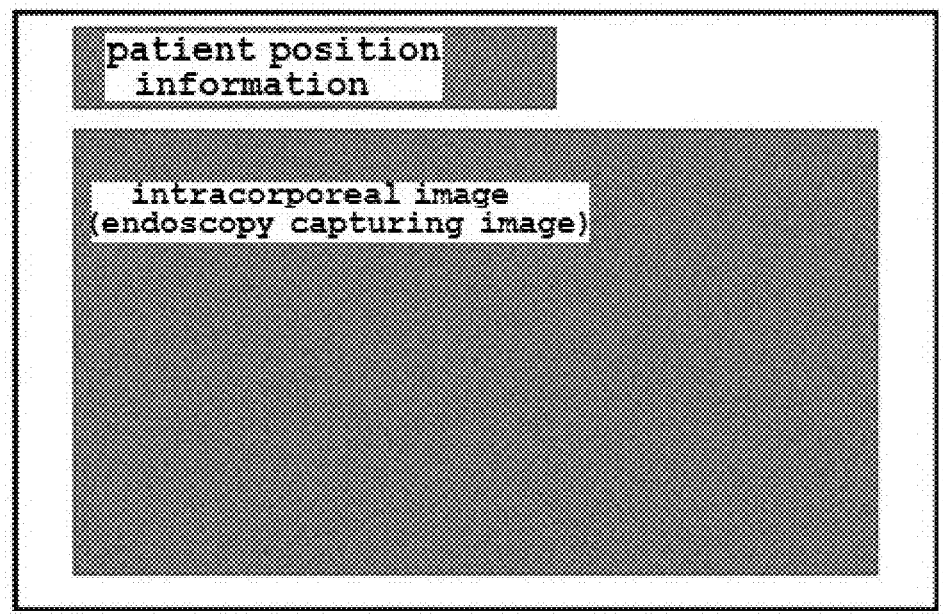
FIGS. 3a to 3c are schematic views showing different implementations of screen displayed on the display device included in the image integrated monitoring apparatus shown in FIG. 1.
Figure 3B:
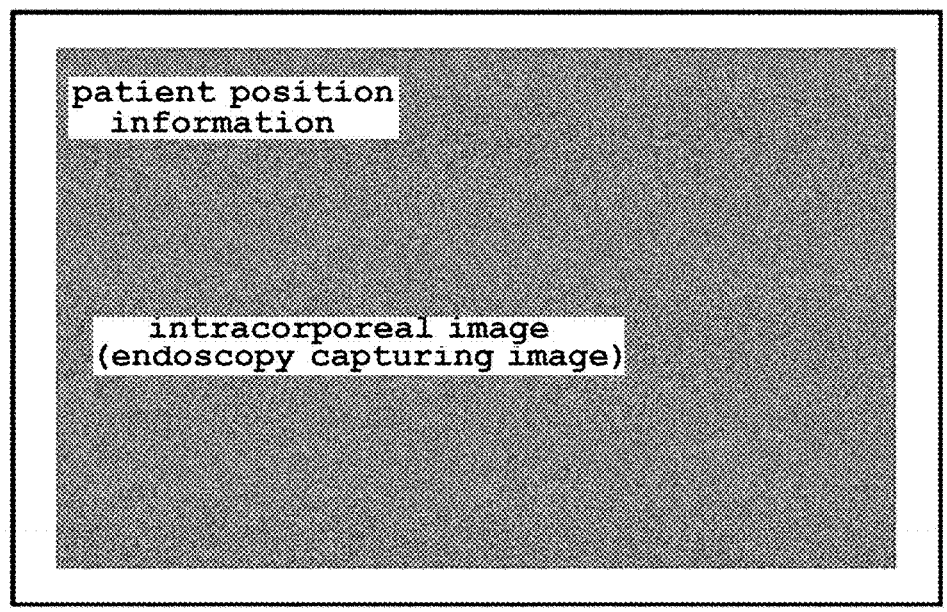
Figure 3C:
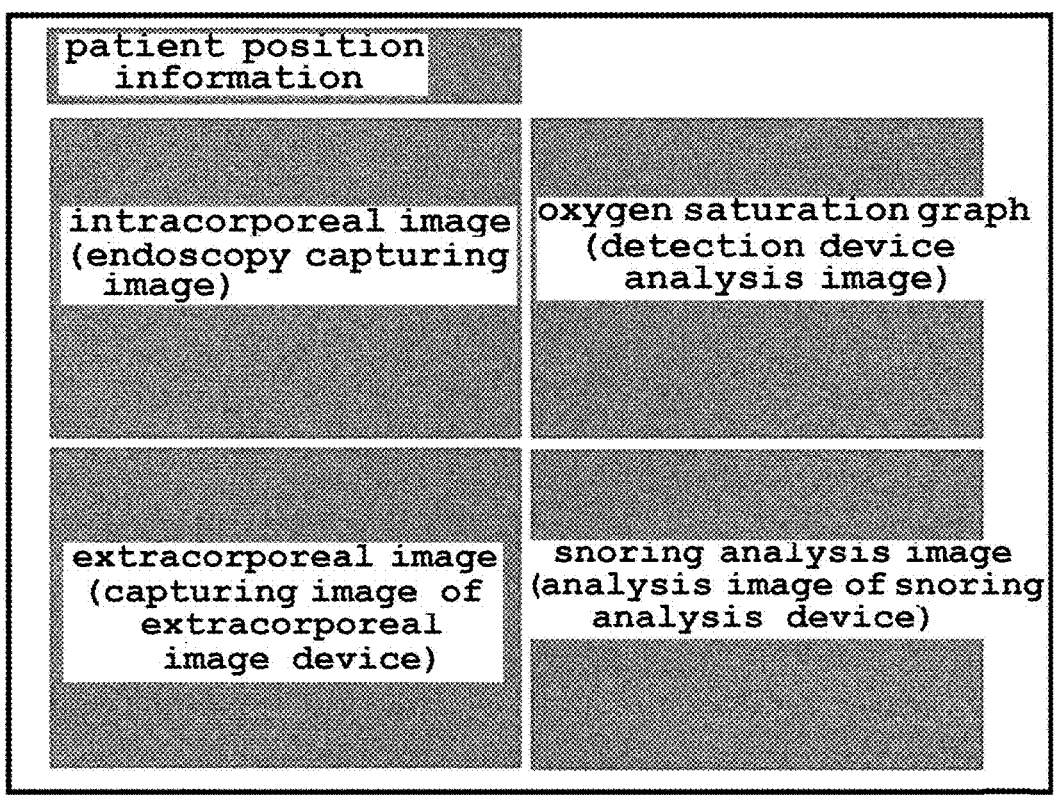
Figure 4A:
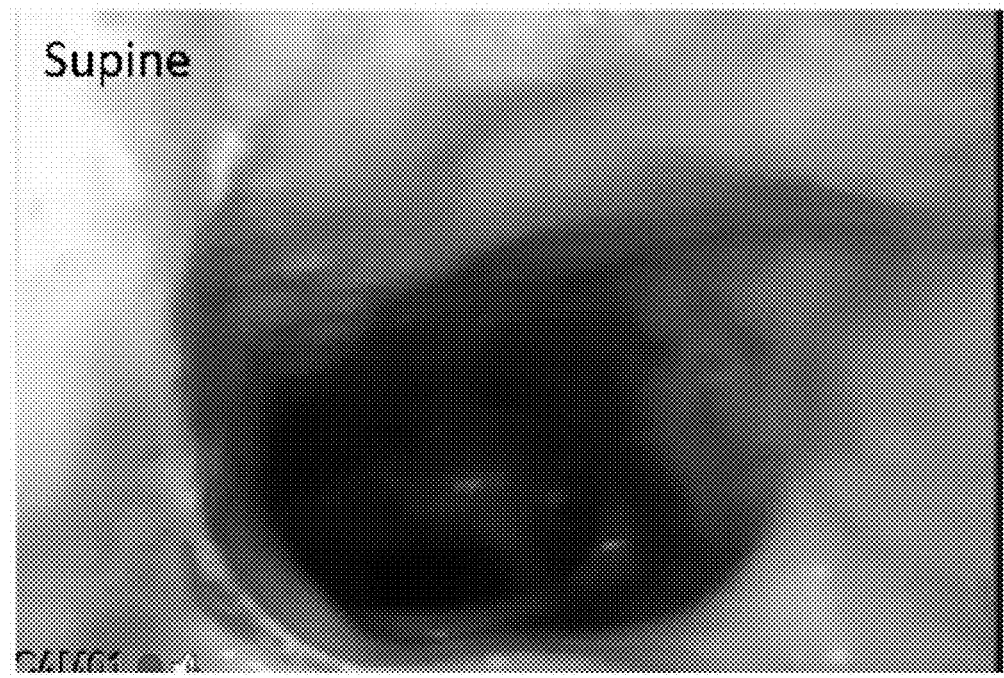
FIG. 4a shows a schematic diagram obtained by actually implementing FIG. 3b.
Figure 4B:
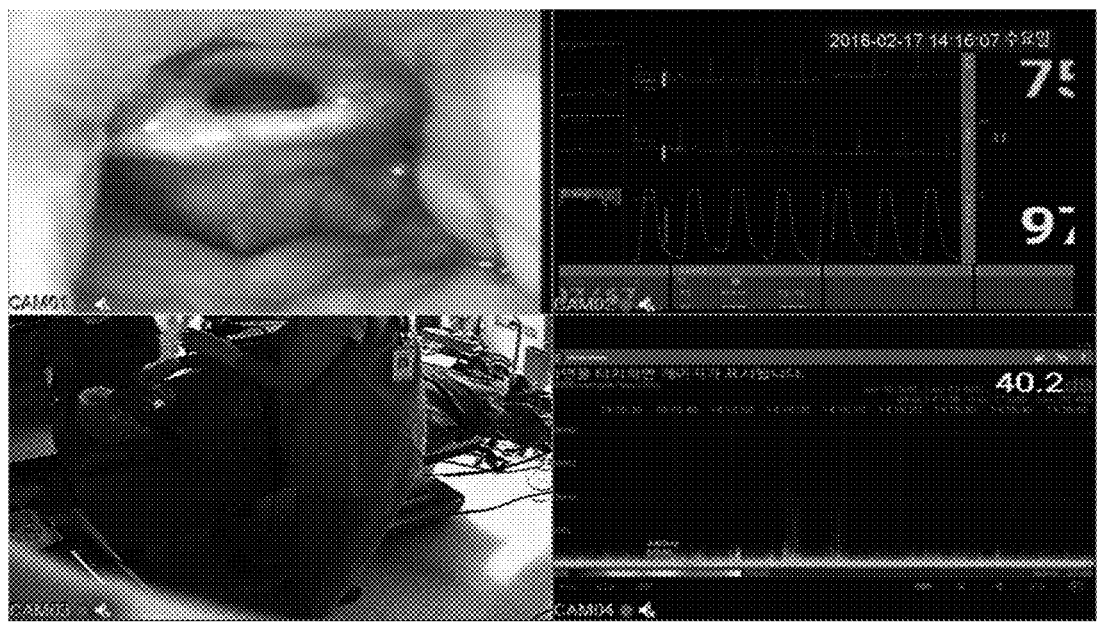
FIG. 4b is a real picture obtained by actually implementing FIG. 3c.

FIG. 1 is a block diagram of a monitoring and diagnosing system according to an embodiment of the present invention, FIG. 2a is a flowchart of an implementation example illustrating a predetermined patient position information protocol to be instructed by a position indication instruction device in the monitoring and diagnosing system of the present invention, and FIG. 2b is an implementation example of a position indication instruction device instructing that the patient position information is displayed on the display device in a monitoring and diagnosing system according to the predetermined patient position information protocol shown in FIG. 2a. FIGS. 3a to 3c are schematic views showing different implementations of screen displayed on the display device included in the image integrated monitoring apparatus shown in FIG. 1, FIG. 4a shows a schematic diagram obtained by actually implementing FIG. 3b, FIG. 4b is a real picture obtained by actually implementing FIG. 3c, and FIG. 5 is a flowchart illustrating a process of generating a diagnosis file in the system of FIG. 1.

As shown in FIG. 1, the monitoring and diagnosing system 100 according to the present invention includes a position indication instruction device 110, endoscope equipment 120, an extracorporeal image capturing device 140, an image integrated monitoring device 130, a snoring analysis device 150, and the detection device 160. As necessary, the monitoring and diagnosing system 100 may be implemented except one or more of the extracorporeal image capturing device 140, the snoring analysis device 150, and the detection device 160, or may include separately a physician behavior monitoring device.

First, the position indication instruction device 110 performs a function of instructing that the patient position information necessary for the drug-induced sleep endoscopic procedure is displayed on a portion of the display device 133 of an image integrated monitoring device 130 during the drug-induced sleep endoscopic procedures that should be performed several times for each body position while changing the patient position.

As such, the position indication instruction device 110 sequentially provides the patient position information to be displayed on the display device 133 according to a predetermined order so that the doctor performing the drug induced sleep endoscopy may perform the endoscopy on each patient body position without exception, and is controlled such that when the start signal is input by the physician performing the drug induced sleep endoscopy, the first patient position information required for the drug induced sleep endoscopy is displayed according to the predetermined order, and when the next signal is input, the patient position information in a next order is sequentially displayed.

Therefore, in order to accurately diagnose sleep-disordered breathing, in a state that the patient takes a plurality of specific body positions, all the intracorporeal images obtained by capturing the patient's upper airway using the endoscope equipment for each body position should be monitored. Here, the position indication instruction device 110 according to the present invention may clearly solve problems that there is a body position that the physician performing drug induced sleep endoscopy ignores and thus does not capture or the intracorporeal image does not match the patient body position during the drug-induced sleep endoscopic procedure in the related art. At the same time, the physician performing drug induced sleep endoscopy may clearly recognize that the intracorporeal image currently being captured by the endoscope equipment and displayed on the display device 133 is obtained from what body position the patient is in. Accordingly, when the procedural physician and an operational surgeon are the same to each other, there is an advantage of immediately identifying the patient's problem during drug induced sleep endoscopy.

The patient position information necessary for diagnosing sleep-disordered breathing through drug induced sleep endoscope in the monitoring and diagnosing system 100 according to the present invention is one selected from a group consisting of Supine (posture of a patient lying down looking at the ceiling), Chin lift & jaw thrust (posture of a patient lifting chin and thrusting jaw), Head turning to left (posture of a patient turning head to left), and Head turning to right (posture of a patient turning head to right). Here, the intracorporeal images captured at four patient body positions are required for accurate diagnosis of sleep-disordered breathing. Therefore, with respect to the predetermined patient position information displayed on the display device 133 by the position indication instruction device 110 of the present invention, an order thereof does not matter as long as the four patient body positions described above are included. However, in consideration of the convenience of the procedural physician and the patient, the order may proceed according to the patient position information protocol for drug induced sleep endoscopy as shown in FIG. 2a.

In addition, the position indication instruction device 110 is an input means that is electrically connected with the monitoring and diagnosing system 100 to send and receive signals with each other and is implemented so that the procedural physician makes a physical contact and sends a signal. As shown in FIG. 2b, the input means may be configured as a foot switch so that the procedural physician performing drug induced sleep endoscopy send instructions by stepping on the same as shown in FIG. 2b. The foot switch may be configured with multiple switches for each body position, but only one switch is configured so that a start signal may be input when the switch is pressed first, and the predetermined patient position information may be sequentially displayed whenever the switch is pressed. As necessary, an input means for instructing that one or more diagnostic files are formed with a test file may be further included.

The endoscope equipment 120 is inserted into the body cavity of the patient taking a position appropriate for the patient position information displayed on the display device serves to capture an intracorporeal image of the patient. In addition, the endoscope equipment 120 includes a capturing means in a tip thereof and is inserted into the human upper airway to collect intracorporeal image information and transmit the collected intracorporeal image information to the outside. Here, the endoscope equipment may include a bronchoscope, an esophagoscope, a gastroscope, a duodenoscope, a rectoscope, a cystoscope, or a laparoscope. In addition, the scope is provided so that the tip thereof is inserted into the patient undergoing the examination and the reflection light obtained by reflecting the light from a light source device is photoelectrically converted by a solid-state image sensor such as a CCD to output the resulting to one or more of the observation monitor of the endoscope equipment 120 or the display device 133 of the image integrated monitoring device. Although not shown, the scope is provided with a scope switch that is assigned a function such as a release switch that instructs the input of images in order to capture the image at a point of time necessary for diagnosis and store the same as a diagnostic file while performing the examination.

As an embodiment, the endoscope equipment 120 includes a light source that emits illumination light for irradiating a part in the body cavity of the human body through a scope, an image processing means for generating an intracorporeal image by performing a variety of signal processing on the observation image of the part in the body cavity obtained by emitting the illumination light from the light source, and an observation monitor for displaying the intracorporeal image. At the same time, the endoscope equipment 120 is provided so that the intracorporeal image obtained by converting the observation image of a subject captured with a scope into the image signal is output, in wire and wirelessly, to the display device 133 of the image integrated monitoring device 130 and stored in the storage means 132. If necessary, the observation monitor may be excluded from the endoscope equipment 120, and the intracorporeal image obtained from the endoscope equipment 120 may be stored in one or more of the storage means 132 of the image integrated monitoring device 130 or the hospital server.

The image integrated monitoring device 130 performs functions of receiving the patient position information to display the patient position information on a partial region of the display device 133 and then receiving the intracorporeal image to output the intracorporeal image on a region excluding or including the partial region of the display device 133, thereby displaying the intracorporeal image and the patient position information to be simultaneously recognized and storing the intracorporeal image and the patient position information as a test file to be simultaneously recognized. The image integrated monitoring device 130 includes a control means 131, a storage means 132, and a display device 133. In some cases, in order to enable immediate treatment to a patient who is in apnea during sleeping, the image integrated monitoring device 130 further includes a warning means of a known configuration that informs the procedural physician that the patient is in apnea state.

In particular, the control means 131 may control the image integrated monitoring device 130, the endoscope equipment 120, and the position indication instruction device 110 so that the procedural physician simultaneously recognizes the patient position information and the intracorporeal image on the display device 133 and stores the same as a test file in the storage means 132. That is, the control means 131 performs control so that the patient's intracorporeal image captured by the endoscope equipment 120 is output on a partial screen on the display device 133 as shown in FIG. 3a or is output to be overlapped as shown in FIG. 3b, in a state that the patient position information is received and displayed on a partial region of the display device, whereby the patient position information and the intracorporeal image are stored as a test file in the storage means 132 to be simultaneously recognized. As necessary, the control means 131 is connected to a an extracorporeal image capturing device 140 to control the extracorporeal image capturing device 140 so as to perform capturing at the same point of time as a point of time when the patient position information and the intracorporeal image displayed on the display device 133 are captured, thereby displaying the intracorporeal image and the extracorporeal image on divided regions of one screen of the display device 133 as shown in FIG. 3c by, and storing the patient position information and the intracorporeal image, and the extracorporeal image as a test file in the storage means 132 to be simultaneously recognized.

In addition, the control means 131 is connected to a snoring analysis device 150 to perform control so that any one or more of a snoring analysis image obtained by allowing the snoring analysis device 150 to analyze a sound recorded at a point of time when the intracorporeal image is captured and the patient position information displayed on the display device 133, a vital sign analysis image analyzed in connection with the detection device 160, and a procedure physician behavior image captured by the monitoring device (not shown) is output on a quad screen on the display device 133 as shown in FIGS. 3c and 4b. Here, the patient position information and the intracorporeal image as well as the snoring analysis image, etc. may be stored in the storage means 132 as a test file to be matched with each other to be simultaneously recognized.

In addition, the control unit 131 stores all the images obtained during the drug-induced sleep endoscopic procedure as a test file, or generates and stores the image at a point of time necessary for sleep-disordered breathing diagnosis as a separate diagnosis file within a predetermined time period (within 60 seconds) starting from a point of time when the input signal is received according to the determination of the physician performing the drug induced sleep endoscopy without saving all the images. The diagnostic file may include one or more of the intracorporeal image, and the patient position information and the extracorporeal image to be matched with each other at a point of time when an input signal is received and/or for a predetermined time, and further include the snoring analysis image, the vital sign analysis image, etc. corresponding to the point of time. When all images obtained during the drug-induced sleep endoscopic procedure are not saved as a test file, the test file may consist of more than one diagnostic file. In this way, when the diagnosis file is generated separately from the test file or as a test file consisting of only one or more diagnostic files, there is an advantage of checking images required to diagnose the patient and explain the diagnosis result to the patient do not need without observing all the images captured during the drug-induced sleep endoscopic procedure to diagnose and operate sleep-disordered breathing. In addition, the control means 131 may be connected to the detection device 160 to control the warning means (not shown) so that a signal is received from the detection device to generate a light or sound so that the procedural physician may know the abnormality of the patient, when the detection device detects abnormalities in vital sign of a patient undergoing drug induced sleep endoscopy, such as apnea occurrence in the patient who is sleeping.

The storage means 132 receives a variety of signal processing data and matches two or more signal processing data to each other to store the same as a storage file, the storage file including the patient position information signal input from the position indication instruction device, the intracorporeal image signal obtained from the endoscope equipment 120, the extracorporeal image signal obtained from the extracorporeal image capturing device 140, the physician behavior image signal obtained from the monitoring device, and the snoring analysis image signal obtained from the snoring analysis device 150, and the vital sign detection signal obtained from the detection device 160. In particular, the storage means 132 stores the diagnostic file generated by the control means 131.

The display device 133 is output by dividing any one or more of the patient position information and intracorporeal image, as well as the extracorporeal image, the snoring analysis image, the vital sign analysis image, the physician behavior image on one screen under the control of the control means 131, thereby allowing the physician to make an effective diagnosis.

Meanwhile, the warning means may be implemented to be visually recognized by the physician performing the drug induced sleep endoscopy using a known configuration, or implemented using a known configuration to be audibly recognized by mounting a separate speaker.

The extracorporeal image capturing device 140 is to capture an extracorporeal image including a change in the patient's body position occurring in correspondence with a part in the upper airway where the endoscope equipment 100 is located during drug-induced sleep endoscopic procedure. If necessary, the extracorporeal image capturing device 140 may be implemented to capture not only the change of the patient's body position, but also the physician behavior image including the behavior change of the physician performing drug induced sleep endoscopy.

Therefore, since the extracorporeal image capturing device 140 is to record and observe one or more of the physician's behavioral change or the patient's position change, any known capturing means may be used so long as extracorporeal image capturing device 140 is implemented to be installed at a location where the physician or patient may be captured to transmit the capturing images to the monitoring device 130.

As an embodiment, the extracorporeal image capturing device 140 is connected to the image integrated monitoring device 130 in a wired or wireless manner so that images of the physician or patient are captured to correspond to the intracorporeal image at the point of time when the endoscope equipment 120 is inserted into the upper airway to capture the body cavity under the control of the control means 131, and the captured extracorporeal images are stored in the storage means 132 to output the same to the display device 133. Here, the installation position of the extracorporeal image capturing device 140 is not limited as long as the extracorporeal image capturing device 140 is installed at a location that allows one or more of the physician and patient to be captured, but may be installed on the top of the display device 133 in view of simplifying the system installation.

The snoring analysis device 150 records a snoring sound of a patient undergoing drug induced sleep endoscopy and generates a waveform. In one embodiment, the snoring analysis device 150 may be a voice analysis device with a microphone. That is, the snoring analysis device 150 may be implemented to amplify the breathing and snoring sounds of the patient who falls in the sleep state through the microphone, record and store even minute sounds, analyze the recorded sounds to generate a waveform, and transmit the generated waveform image to the image integrated monitoring device 130.

The detection device 160 detects a vital sign of a patient undergoing endoscopy, and may be implemented to detect at least oxygen saturation and electrocardiogram. That is, the detection device 160 may be all the detection devices having a known configuration, as long as the detection device 160 includes a sensing means, such as various sensors, for sensing a vital sign and an analysis means for analyzing a signal detected by the sensing means.

Meanwhile, the monitoring and diagnosing system 100 of the present invention includes the position indication instruction device 110, the endoscope equipment 120, the image integrated monitoring device 130, and the extracorporeal image capturing device 140, the snoring analysis device 150, and the detection device 160 as shown in FIG. 1, each of these components may be implemented as a single unit, or may be implemented separately.

For example, when the monitoring and diagnosing system of the present invention is implemented by utilizing endoscope equipment, a snoring analysis device, and a detection device that have been already purchased separately in a hospital, the position indication instruction device and/or the extracorporeal image capturing device may be further installed in addition to the respective devices so that monitoring may be implemented by integrating monitor the image signals obtained from each component as described above through the image integrated monitoring device 130.

In addition, when the monitoring and diagnosing system 100 of the present invention is implemented to be integrated as a device, the monitoring and diagnosing system 100 may be implemented so that each of the above components is connected to one main body and the control means 131 controls all the components to perform each function.

Operations of the drug induced sleep endoscopy in the monitoring and diagnosing system 100 having the above-described configuration according to the present invention will be described.

In performing drug induced sleep endoscopy test, the physician performing the endoscopic examination inputs patient's identification information, such as a test ID added to the endoscopy test or an ID number of the patient performing the test from an input device such as a keyboard or a card reader of the endoscope equipment 120 or the image integrated monitoring device 130 in the monitoring and diagnosing system 100 installed next to the patient's bed (when the patient is not registered on the server, the patient's personal information such as name, age, and gender are also input). When such an input is present, the image integrated monitoring device 130 reads personal information about the patient from the server to generate header information that is added to storage files for patient position information, intracorporeal image from the endoscope equipment, and other images matching the intracorporeal images input during drug-induced sleep endoscopic procedure and/or diagnostic file that is composed of important image including patient position information, an intracorporeal image and/or an extracorporeal images at a certain time of point which are particularly important for diagnosis.

Then, when the procedure physician presses the position indication instruction device 110 implemented in the form of a foot switch in order to proceed the drug induced sleep endoscopy according to the preset patient position information protocol, Supine is displayed as first spatial position information on the display device 133 according to the input signal as shown in FIG. 2a. The physician checks whether the patient position information displayed on the display matches the actual position of the patient, and captures an intracorporeal image by inserting the endoscope equipment into the body cavity, specifically a nasal cavity, of the patient taking a position appropriate for the patient position information. A drug-induced sleep endoscopic procedure step may be performed so that the intracorporeal image taken from the endoscope equipment in Supine, which is the first patient body position, is displayed separately from or to be overlapped with the patient position information already displayed on the display device, and the intracorporeal image and the patient position information are matched with each other and stored as an examination file in the storage means 132 so as to be simultaneously recognized. Herein, the drug-induced sleep endoscopic procedure step may be performed by further including one or more of the following steps. First, the extracorporeal image capturing device captures, as extracorporeal image, a specific positional change of the patient that occurs in correspondence with a point of time when the endoscope equipment takes a specific part in the upper airway as an intracorporeal image, and here the captured extracorporeal image may be displayed on the display device to be matched with the first spatial position information and the intracorporeal image to be recognized simultaneously, and may be stored as a test file to be recognized simultaneously with the first spatial position information and the intracorporeal image. In addition, the snoring analysis device obtains a snoring analysis image by recording the snoring sound of the patient generated in correspondence with a point of time when the endoscope equipment captures a specific part in the upper airway as the intracorporeal image, and the snoring analysis image may be displayed on the display device so as to be recognized simultaneously with the intracorporeal image and the first spatial position information, and may be stored as a test file to be simultaneously recognized. In addition, the detection device generates a vital sign analysis image by detecting the bio-signal of the patient that occurs in correspondence with a point of time when the endoscope equipment captures a specific part of the upper airway as an intracorporeal image, and the generated vital sign analysis image may be displayed on the display device to be recognized simultaneously with the intracorporeal image and the first spatial position information, and may be stored as a test file to be simultaneously recognized. Then, when the physician manipulates the scope while viewing the endoscope image, that is, the patient position information and the intracorporeal image displayed on the display device 133 of the image integrated monitoring device 130 and presses the release switch or the switch of the integrated image monitoring device installed in the scope at a point of time when it is determined to be necessary for diagnosis by the physician, the image integrated monitoring device 130 may generate diagnostic files by receiving the intracorporeal image captured with endoscope equipment for a predetermined period of time (within 60 seconds) starting from the point of time under the control of the control means 131, as well as the extracorporeal images, the snoring analysis images, and the vital sign analysis images matched at the point of time, for example, as a still image, as shown in FIG. 5. In this way, the test file and one or more diagnostic files are generated, but in some cases, the test file itself may be composed only of one or more diagnostic files. The generated test file and/or diagnostic file are subjected to data compression processing, and are stored in any one or more of the storage means 132 or the hospital server after adding the header information including the personal information of the patient or the photographing information of the image to the compressed image data. Thereafter, the process shown in FIG. 5 may be repeated until the endoscopy is finished. Herein, a plurality of diagnostic files for a patient may be stored as a single diagnostic file.

Meanwhile, when the drug-induced sleep endoscopic procedure step is completed in the first body position, the physician presses the position indication instruction device 110 again so that the display device 133 displays the Chin lift & jaw thrust (posture of a patient lifting chin and thrusting jaw) as the second spatial body position according to the signal input from the position indication instruction device 110. Then, the physician instructs the patient to take the second spatial body position and operates the monitoring and diagnosing system, i.e., operates the endoscope equipment 120, the image integrated monitoring device 130, and one or more of the extracorporeal image capturing device 140, the snoring analysis device 150, and the detection device 160, to repeat the drug-induced sleep endoscopic procedure steps as shown.

The drug-induced sleep endoscopic procedure steps described above are repeated until the last patient position information, that is, the fourth patient position information, is displayed while changing the position of the patient according to the patient position information displayed on the display device.

When the drug induced sleep endoscopy test is performed through the monitoring and diagnosing system 100 according to the present invention, it is possible to check simultaneously, on one screen, the patient position information and the state of the airway obstruction part of the patient during the drug induced sleep endoscopy test, the vital sign of the patient such as oxygen saturation, the phonetic characteristics and the change in the patient's body position at the time of snoring and sleep apnea event, and the like, and it is possible to store the same as test files to be simultaneously recognized and create a separate diagnosis file for a specific point of time, thereby reproducing and checking the later test, and facilitating the establishment of treatment methods and explanations to patients and doctors.

In other words, the physician can make a surgical plan or check patient symptoms and explain the same to the patient while viewing only one or more diagnostic files generated by obtaining only the image that is determined to be important for diagnosis by the physician during the drug-induced sleep endoscopic procedure, whereby there are a variety of benefits to both doctors and patients.

Although the present invention has been shown and described with reference to the preferred embodiments as described above, the present invention is not limited to the above embodiments and various changes and modifications may be made by those skilled in the art to which the present invention pertains without departing from the spirit of the present invention.

The invention claimed is:

1. A monitoring and diagnosing system, comprising:
a position indication instruction device instructing to display patient position information necessary for a drug-induced sleep endoscopic procedure on a partial region of a display device during the drug-induced sleep endoscopic procedure, that is to be performed several times for each position while changing a patient body position;
an endoscope equipment inserted into an upper airway of a patient taking a body position suitable for the patient position information displayed on the display device to capture an intracorporeal image of the patient; and
an image integrated monitoring device receiving the patient position information to display the patient position information on a partial region of the display device and then receiving the intracorporeal image to output the intracorporeal image on a region including or excluding the partial region of the display device, thereby displaying the intracorporeal image and the patient position information to be simultaneously recognized and storing the intracorporeal image and the patient position information as a test file to be simultaneously recognized.

2. The system of claim 1, wherein the position indication instruction device is controlled so that first patient position information required for the drug-induced sleep endoscopic procedure is displayed according to a predetermined order when a start signal is input by a procedural physician performing the drug induced sleep endoscopy and next patient position information is sequentially displayed when a next signal is input.

3. The system of claim 1, wherein the position indication instruction device is configured as a foot switch stepped on by a procedure physician performing the drug induced sleep endoscopy.

4. The system of claim 1, wherein the patient position information is one selected from a group consisting of Supine (posture of a patient lying down looking at a ceiling), Chin lift & jaw thrust (posture of a patient lifting chin and thrusting jaw), Head turning to left (posture of a patient turning head to left), and Head turning to right (posture of a patient turning head to right).

5. The system of claim 1, further comprising:
an extracorporeal image capturing device capturing, as an extracorporeal image, a specific change in the patient body position occurring in correspondence to a point of time when the endoscope equipment captures a specific part in the upper airway as the intracorporeal image.

6. The system of claim 5, wherein the image integrated monitoring device receives the extracorporeal image from the extracorporeal image capturing device to output and display the extracorporeal image for the change in the patient body position simultaneously on the display device to be corresponded to the intracorporeal image of the specific part in the upper airway, and stores the intracorporeal image, the extracorporeal image, and the patient position information as a test file to be simultaneously recognized.

7. The system of claim 1, further comprising:
a snoring analysis device recording a snoring sound of the patient undergoing the drug induced sleep endoscopy and generating a waveform to form a snoring analysis image.

8. The system of claim 1, further comprising:
a detection device detecting and analyzing a vital sign of the patient during the endoscopic procedure.

9. The system of claim 8, wherein the detection device detects and analyzes one or more of oxygen saturation and electrocardiogram.

10. The system of claim 1, further comprising:
a monitoring device capturing a physician behavior image including behavioral changes of the procedural physician performing the drug induced sleep endoscopy.

11. The system of claim 1, wherein the image integrated monitoring device further receives one or more of the intracorporeal image, any one or more of the patient position information and the extracorporeal image, a physician behavior image of the procedural physician performing the drug induced sleep endoscopy, and a snoring analysis image and a vital sign analysis image of the patient undergoing the drug induced sleep endoscopy to be outputted on the display device simultaneously.

12. The system of claim 1, wherein the image integrated monitoring device receives an input signal according to a determination of the procedural physician performing the drug induced sleep endoscopy and then stores the test file as one or more diagnostic files including images at a point of time necessary for sleep-disordered breathing diagnosis.

13. The system of claim 12, wherein the diagnostic file includes any one or more of the intracorporeal image, the patient position information, and the extracorporeal image corresponding to a point of time when the input signal is received.

14. The system of claim 1, further comprising:
when apnea occurs in a patient who is sleeping during the drug-induced sleep endoscopic procedure, a warning unit informing the physician performing the procedure that the patient is in apnea to treat the patient immediately.

15. A monitoring and diagnosing method of sleep-disordered breathing, the method comprising:
a drug-induced sleep endoscopic procedure step including displaying predetermined patient position information on a display device according to a signal input from a position indication instruction device, displaying an intracorporeal image captured by endoscope equipment in an upper airway of a patient taking a position appropriate for the patient position information, separately from or to be overlapped with the patient position information on the display device, and storing the intracorporeal image and the patient position information as a test file to be recognized simultaneously; and
repeating the drug-induced sleep endoscopic procedure step a number of times that is one less than the number of pieces of the predetermined patient position information according to an order of the predetermined patient position information.

16. The method of claim 15, wherein the drug-induced sleep endoscopic procedure step further includes:
capturing, as an extracorporeal image, a specific change of a patient position occurring in correspondence to a point of time when the endoscope equipment captures a specific part in the upper airway as the intracorporeal image, by an extracorporeal image capturing device; and
displaying the captured extracorporeal image on the display device to be recognized simultaneously with the intracorporeal image and storing the captured extracorporeal image as the test file to be recognized simultaneously with the intracorporeal image.

17. The method of claim 15, wherein the drug-induced sleep endoscopic procedure step further includes:
recording a snoring sound of a patient occurring in correspondence to a point of time when the endoscope equipment captures a specific part in the upper airway as the intracorporeal image and generating a waveform to obtain a snoring analysis image, by a snoring analysis device; and
displaying the snoring analysis image on the display device to be recognized simultaneously with the intracorporeal image and the patient position information and storing the snoring analysis image as the test file to be recognized simultaneously with the intracorporeal image and the patient position information.

18. The method of claim 15, wherein the drug-induced sleep endoscopic procedure step further includes:
detecting and analyzing a vital sign of a patient occurring in correspondence to a point of time when the endoscope equipment captures a specific part of the upper airway as the intracorporeal image to generate a vital sign analysis image, by a detection device; and
displaying the generated vital sign analysis image on the display device to be recognized simultaneously with the intracorporeal image and the patient position information, and storing the generated vital sign analysis image as the test file to be recognized simultaneously with the intracorporeal image and the patient position information.

19. The method of claim 15, wherein the test file is a diagnostic file including the intracorporeal image, and any one or more of the position indication information and the extracorporeal image, which correspond to a point of time when an input signal is received according to a determination of a procedure physician performing the drug induced sleep endoscopy.

* * * * *